(12) United States Patent
Hachiya et al.

(10) Patent No.: US 7,736,894 B2
(45) Date of Patent: Jun. 15, 2010

(54) METHOD FOR CONSTRUCTING RECONSTRUCTED SKIN

(75) Inventors: Akira Hachiya, Tochigi (JP); Eiko Kaiho, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/847,380

(22) Filed: May 18, 2004

(65) Prior Publication Data

US 2005/0043795 A1    Feb. 24, 2005

(30) Foreign Application Priority Data

May 23, 2003   (JP)   ............... 2003-146637

(51) Int. Cl.
*C12N 5/00*   (2006.01)
(52) U.S. Cl. ............... 435/373; 623/15.12; 424/423
(58) Field of Classification Search .............. None
See application file for complete search history.

(56) References Cited

U.S. PATENT DOCUMENTS 5,702,945 A * 12/1997 Nagels et al. ............ 435/297.1
6,040,493 A *  3/2000 Cooke et al. ............... 602/41

FOREIGN PATENT DOCUMENTS

| JP | 1-122723 | 8/1989 |
| JP | 3-116830 | 12/1991 |
| JP | 2002-505859 | 2/2002 |
| WO | 99/45770 | 9/1999 |

OTHER PUBLICATIONS

Bell et al, "Living Tissue Formed in vitro and Accepted as Skin-Equivalent Tissue of Full Thickness", Science, 1981, vol. 211, No. 4486, pp. 1052-1054.*
Bell et al, "The Reconstitution of Living Skin" Journal of Investigative Dermatology, 1983, vol. 81 Suppl. pp. 2s-10s.*
Boyce et al, "Pigmentation and Inhibition of Wound Contraction by Cultured Skin Substitutes with Adult Melanocytes After Transplantation to Athymic Mice" Journal of Investigative Dermatology, 1993, vol. 100, pp. 360-365.*
Prunieras et al, "Methods for Cultivation of Keratinocytes with an Air-Liquid Interface" Journal of Investigative Dermatology, 1983, vol. 81, No. 1 Supplement 1, pp. 28s-33s.*
Berking et al, "Photocarcinogenesis in human adult skin grafts" Carcinogenesis, 2002, vol. 23, No. 1, pp. 181-187.*
Makoto Tsunenaga, et al., "Organotypic Culture of Human Keratinocytes", Tissue Culture, vol. 20, No. 8, 1994, pp. 282-285 (with English partial translation).
Makoto Tsunenaga, et al., "Growth and Differentiation Properties of Normal and Transformed Human Keratinocytes in Organotypic Culture". Jpn. J. Cancer Res., vol. 85, No. 3, Mar. 1994, pp. 238-244.

(Continued)

*Primary Examiner*—Allison M Ford
(74) *Attorney, Agent, or Firm*—Oblon, Spivak, McClelland, Maier & Neustadt, L.L.P.

(57) ABSTRACT

The present invention relates to a method for constructing human skin tissue, in which human skin tissue is reconstructed on a body surface of an immunodeficient non-human animal.

14 Claims, 10 Drawing Sheets

OTHER PUBLICATIONS

Homg-Chin Yan, et al., "Human/Severe Combined Immunodeficient Mouse Chimeras an Experimental in Vivo Model system to Study the Regulation of Human Endothelial Cell-Leukocyte Adhesion Molecules", The American Society for Clinical Investigation, Inc., vol. 91, No. 3, Mar. 1993, pp. 986-996.

C. Kathy Wang, et al., "Spontaneous Cell Sorting of Fibroblasts and Keratinocytes Creates an Organotypic Human Skin Equivalent", The Society for Investigative Dermatology, Inc., vol. 114, No. 4, Apr. 2000, pp. 674-680.

Steven T. Boyce, et al., "Vitamin C Regulates Keratinocyte Viability, Epidermal Barrier, and Basement Membrane in Vitro, and Reduces Wound Contraction After Grafting of Cultured Skin Substitutes", The Society for Investigative Dermatology, Inc., vol. 118, No. 4, Apr. 2002, 565-572.

Fusenig, N. E., et al., "Growth and Differentiation Characteristics of Transformed Keratinocytes from Mouse and Human Skin in Vitro and in Vivo," The Journal of Investigative Dermatology, vol. 81, No. 1, Supplement, Jul. 1983, pp. 168s-175s.

Lichti, U., et al., "In Vivo Regulation of Murine Hair Growth: Insights from Grafting Defined Cell Populations onto Nude Mice," The Journal of Investigative Dermatology, vol. 101, No. 1, Supplement, Jul. 1993, pp. 124S-129S.

Yuspa, S. H., et al., "The Growth of Fetal Mouse Skin in Cell Culture and Transplantation to $F_1$ Mice," The Journal of Investigative Dermatology, vol. 55, No. 6, 1970, pp. 379-389.

* cited by examiner 4.a                    4 b (A)   (B)

Epidermis     Dermis

Light (A)

(B)

(A)

(B)

(A)

(C)

(B)

(D)

US 7,736,894 B2

METHOD FOR CONSTRUCTING RECONSTRUCTED SKIN

FIELD OF THE INVENTION

The present invention relates to a method for constructing human skin tissue using experimental animals.

BACKGROUND OF THE INVENTION

In recent years, attention has been paid to regenerative medicine and regenerative medical care. Regenerative medical care is a type of medical care which by using cells attempts to regenerate the functions of biological tissues and organs which have fallen into functional disorder and dysfunction. In the field of regenerative medicine, almost all organs and tissues are targets for research, and they have already been put to practical use in some areas. Among them, an organ for which a technology for reconstructing self-regenerating tissues and organs has first been established is skin.

In the research field, regenerated skin in an in vitro system has so far been most widely used as a skin model because of its good handling property (Bell E, Ehrlich H P, Buttle D J, Nakatsuji T., Science Mar; 211 (4486): 1052-4, 1981, Tsunenaga M, Horii I, Kuroki T, Tissue Culture (20 (8), 282-285, 1994, Tsunenaga M, Kohno Y, Horii I, Yasumoto S, Huh N H, Tachikawa T, Yoshiki S, Kuroki T, Jpn J Cancer Res Mar; 85 (3): 238-44, 1994). However, it has the disadvantages in that the character thereof can be maintained only for a short period and that the durability against medicine is weak. As a human skin model which can be used to solve the above problems, there is technology in which human skin species are grafted directly onto immunodeficient animals (Yan H C, Juhasz I, Pilewski J, Murphy G F, Herlyn M, Albelda S M, J Clin Invest Mar; 91 (3): 986-96, 1993). This model is a skin model which is considerably close to human skin in situ. On the other hand, availability of fresh human skin is an important factor, and actual situations involve a practical problem in terms of available acquisition of fresh human skin.

A method for grafting a cultured human cell onto an immunodeficient animal to construct regenerated skin has been developed in order to overcome the situation described above. There are a plurality of such methods, and among them, attention has been paid to a spontaneous sorting method (for example, Japanese Patent Application Laid-Open (through PCT) No. 50589/2002, Wang C K, Nelson C F, Brinkman A M, Miller A C, Hoeffler W K, J Invest Dermatol. 2000, April; 114 (4): 674-80) in recent years. In this method, primarily cultured keratinocyte isolated from fresh human skin is mixed with a fibroblast to construct reconstructed skin on the skin of an experimental animal. This method provides the advantages that the cell can freely move and interaction between the cells is liable to be caused and that a structure closer to the skin of a living body is available.

However, according to the reports which have so far been given, evaluations are made only for 4 weeks after grafting at the longest, and at the end of this period, at least the surface's state does not reach a smooth state similar to that of human skin. In addition thereto, a decrease in the area of reconstructed skin with the passage of time, which is one of the typical and significant problems in constructing reconstructed skin, has not yet been solved (Boyce S T, Supp A P, Swope V B, Warden G D, J Invest Dermatol 2002 April; 118 (4): 556-7).

SUMMARY OF THE INVENTION

The present invention relates to a method in which a cultured human skin is used to construct reconstructed human skin which is histologically and functionally similar to human skin and which is excellent in terms of quantity and convenience.

That is, the present invention provides a method for constructing a human skin tissue, in which a human skin tissue is reconstructed on a body surface of a non-human animal, which includes:
(a) burying a cell-injectable cylindrical chamber into a dorsal skin of an immunodeficient non-human animal,
(b) injecting a cell suspension containing a cultured human fibroblast and a cultured human keratinocyte into the chamber,
(c) cutting an upper bottom part of the chamber 7 or more days after grafting of the cell to fully open the cylinder part of the chamber, and then
(d) eliminating the chamber.

Further, the present invention provides a method for constructing human skin tissue, in which human skin tissue is reconstructed on a body surface of a non-human animal, which includes:
(a) burying a cell-injectable cylindrical chamber into a dorsal skin of an immunodeficient non-human animal,
(b) injecting a cell suspension containing a cultured human fibroblast, a cultured human keratinocyte and a cultured human melanocyte into the chamber,
(c) cutting an upper bottom part of the above chamber 7 or more days after grafting of the cell to fully open the cylinder part of the chamber, and then
(d) eliminating the chamber.

Also, the present invention provides a human skin tissue obtained by the method described above and an experimental animal carrying a human skin tissue.

Further, the present invention provides a method for screening substances which act on melanocyte by using the animals described above.

Figure 1:
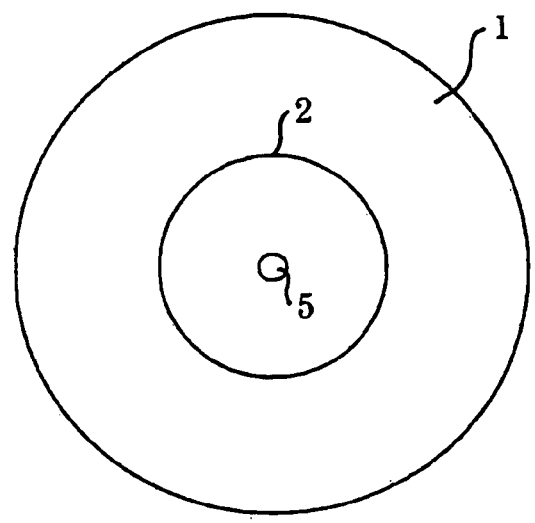
FIG. 1 is an exterior view (front view) of an embodiment of the chamber of the present invention.
Figure 2:
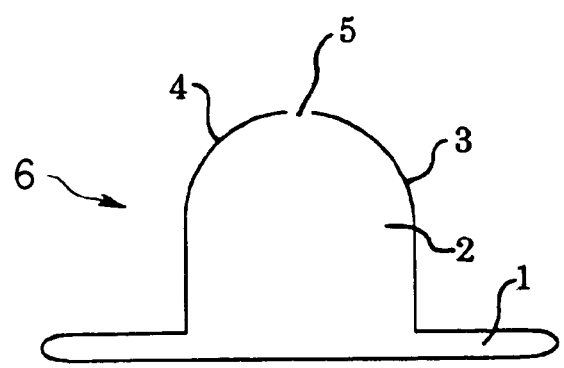
FIG. 2 is an exterior view (cross-sectional view) of an embodiment of the chamber of the present invention.
Figure 3:
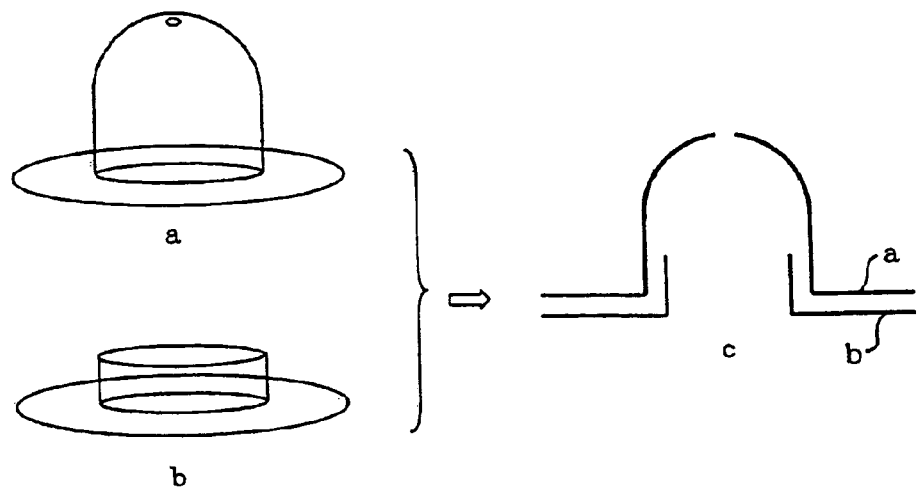
FIG. 3 is a schematic drawing when an upper side chamber "a" and a lower side chamber "b" are used.

Designations shown in FIGS. 1 to 3 represent the following: 1: collar part, 2: cylinder part, 3: upper bottom part, 4: top part, 5: small hole (cell injecting port), a: upper side chamber, and b: lower side chamber, 6: the whole cell-injectable chamber.

DETAILED DESCRIPTION OF THE DRAWINGS

According to the present invention, there can be provided a reconstructed human skin which is excellent in terms of quantity and convenience for researching expression of genes and proteins of human skin and evaluating medicines acting on human skin, particularly on melanocyte.

The present inventors have investigated a method for reconstructing human skin on a skin of an experimental animal and have found that reconstructed human skin which has a smooth gloss similar to that of human skin and which has a fixed or larger size can be constructed by carrying out steps (a) to (c) described above.

The immunodeficient non-human animal used for carrying out the present invention includes, for example, immunodeficient mice such as an SCID mouse, BALBcA-nu/scid and B-17/Icr-Scid and immunodeficient rats such as F344 Jc1-rnu. In particular, the immunodeficient mice described above are preferably used in view of a balance between the cell number used and a size of the chamber and a convenience in burying the chamber and suturing.

These animals are preferably bred under the condition of one head/one cage in the environment of SPF. Such animals are available from Nippon Clear Co., Ltd.

The chamber used in the present invention shall not be restricted as long as it has such a structure that can be buried into the skin of the animal, and includes, for example, cylindrical chambers having a collar part at a lower part and having a structure into which a cell can be injected. Among them, a chamber having a hat form is preferred. The structure into which a cell can be injected includes a structure having an injectable small hole and a structure formed from a material into which an injection needle can penetrate, such as a structure in which a chamber itself is formed from silicon. Another preferred embodiment of a method for constructing reconstructed skin according to the present invention shall be explained below in detail.

FIG. 1 is a plan view of a hat type chamber having a collar at a lower part and having a structure into which a cell can be injected, and FIG. 2 is a cross sectional view thereof. In the chamber of the present invention, preferably upper side chamber "a" and lower side chamber "b" each having the same form are combined as shown in FIG. 3, (FIG. 3c). This embodiment is advantageous in that the chamber is prevented from deviating and in that the cell is prevented from leaking from the chamber.

In FIG. 1 and FIG. 2, 1 represents a collar part, 2 represents a cylinder part, 3 represents an upper bottom part, and 4 represents a top part. A small hole having a diameter of 2 to 4 mm for injecting a cell suspension is provided at the top part.

A material for the above chamber shall not specifically be restricted, and the chamber made of, for example, silicon, Teflon (registered trade mark) or polypropylene can be used. Though the size of the chamber varies depending on the size of the animal used for grafting, the chamber having usually an inner diameter of 7 to 12 mm and an outer diameter of 16 to 24 mm is preferably used.

A commercially available chamber includes upper side chamber "a" (inner diameter 12 mm, outer diameter 24 mm) and lower side chamber "b" (inner diameter 11 mm, outer diameter 24 mm) each shown in FIG. 3, and they can be used by interfitting.

In burying the chamber into the skin of an animal (step (a)), the skin on the back of the animal is cut in a circular form, and the chamber is inserted thereinto. The chamber is fixed with an adhesive or by suturing the skin at the periphery of the chamber just like tightening the string of a bag. The chamber is preferably buried by suturing in view of easiness in elimination of the chamber.

A mixture containing a cultured human fibroblast a cultured human keratinocyte and, if necessary, a cultured human melanocyte is used as the skin cell to be grafted in a preferred method of the present invention.

A cell originating from an adult's skin (breast) and a cell originating from a newborn's skin (foreskin) can be used as the cultured human fibroblast, and they can be obtained by the following method. For example, an epidermis of a foreskin is physically separated from a dermis, and the dermis is finely broken up and cultured in a Dulbecco's modified Eagle's medium (Invitrogen) containing a 10% fetal bovine serum (Invitrogen Corporation). A cell growing from a dermal tissue is a fibroblast. A commercial product, for example, a normal human newborn foreskin fibroblast is purchased, cultured and subcultured, and it can be used as the above cultured human fibroblast.

A cell originating from a human newborn's foreskin can be used as the cultured human keratinocyte. For example, a dermis of the foreskin is physically separated from an epidermis, and the epidermis is finely broken up and left standing (37° C.) in 0.3% trypsin. Then, the trypsin is neutralized, and the epidermis tissue is further finely broken by means of a surgical pincette and filtered through a metal-made mesh to remove the residue. The broken keratinocyte is recovered by centrifugation, and the pellets thereof are suspended in keratinocyte SFM (invitrogen) and cultured in the same culture medium, whereby the cultured human keratinocyte can be obtained. A commercial product, for example, a normal human epidermal cornified cell (Kurashiki Boseki Co., Ltd.) is purchased, cultured and subcultured, and it can be used as the above cultured human keratinocyte.

For example, a cell originating from a human newborn's foreskin is used as the cultured human melanocyte. For example, a dermis of the foreskin is physically separated from an epidermis, and the epidermis is finely broken up and can be isolated by restriction by a culture medium. However, a commercially available cell is preferably used from a practical point of view. A commercial product, for example, a normal human epidermal pigment cell (Kurashiki Boseki Co., Ltd.) is purchased, cultured and subcultured, and it can be used as the above cultured human melanocyte.

The cultured human fibroblast and the cultured human keratinocyte, or the cultured human fibroblast, the cultured human keratinocyte and the cultured human melanocyte each obtained in the manners described above are mixed to prepare a cell suspension, and the suspension is subjected to centrifugal separation to remove the culture medium and obtain only the cells, and the cells are injected into the chamber through the small hole 5 provided at the top part 4 of the chamber by means of a pipette (step (b)). An amount of the cells is preferably 400 to 600 µL/cm$^2$.

Figure 4:
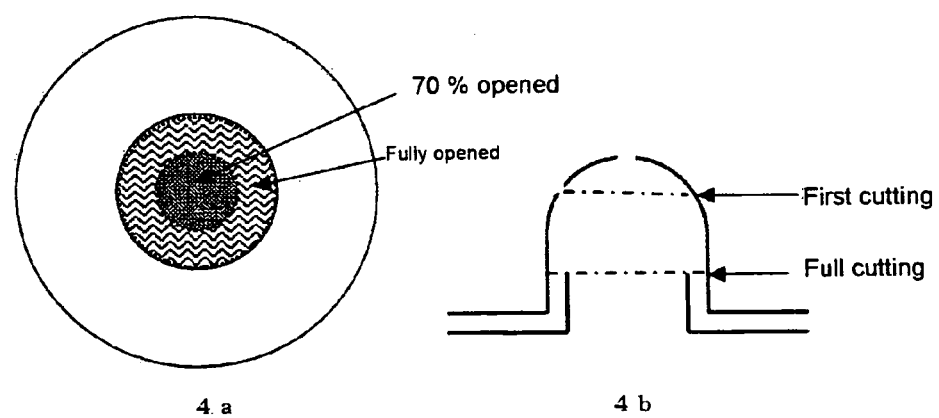
FIG. 4 is a schematic drawing (4a: front view, 4b: cross-sectional view) showing cutting of the upper bottom part of the chamber.

It takes usually 8 to 12 weeks until a tissue having a surface state similar to that of a human skin is reconstructed after starting grafting of a cell. In the method of the present invention, the upper bottom part of the above chamber is cut preferably by the time the chamber is eliminated, that is, 7 or more days after grafting of the cell, more preferably by 7 to 20 days after grafting, whereby the cylinder part is fully opened (step (c), refer to FIG. 4).

The cylinder part of the chamber is preferably gradually opened by several cuttings, whereby rapid drying is prevented and constriction of the reconstructed skin is inhibited. The number of times of cutting is preferably twice considering workability and rapid drying. Preferably, the cylinder part is cut 7 to 10 days, preferably 7 days after grafting to open 60 to 80%, preferably about 70% of a cross-sectional area of the cylinder part of the chamber, and thereafter left standing the cut opened chamber for an additional 7 to 10 days, whereafter the cylinder part is fully opened (refer to FIG. 4a).

When upper side chamber a (inner diameter 12 mm, outer diameter 24 mm) and lower side chamber b (inner diameter 11 mm, outer diameter 24 mm) are used in combination as a chamber, the chamber may be cut at a point about 5 mm below the top part at the first cutting, and after a predetermined period of time, it may be cut (at a point about 8 mm below the top part) so that the cylinder part is fully opened (refer to FIG. 4b).

When a part of the upper bottom part of the chamber is cut to open the cylinder part, a member through which gas can pass is preferably mounted on the above opened part to cover the above opened part from the viewpoints of preventing mixing of bedding materials and preventing quick drying. The above member shall not specifically be restricted as long as gas can pass through it, and it includes, for example, gauzes, nonwoven fabrics, cloths and nets. The nets may be made of any of metals, resins or cotton, and the pore diameter thereof is preferably 0.1 to 0.5 mm, more preferably 0.2 to 0.3 mm.

The chamber is preferably eliminated in about 28 to 56 days, preferably about 28 to 35 days after fully opening the cylinder part of the chamber (step (d)), and after fully opening, a proper amount of moisture is preferably fed in order to prevent the reconstructed skin from rapid drying. In this case, moisture is preferably fed, for example, by dropping a physiological salt solution on the reconstructed skin once every 2 to 4 days in an amount of 400 µL/cm$^2$ by means of a syringe.

The chamber is detached preferably in such a manner that the chamber is spontaneously eliminated from the skin by cutting a suture thread with which the skin of the animal is sutured to fix the chamber when the chamber is buried by suturing, or when the chamber is buried using an adhesive. Thus, the chamber is preferably spontaneously eliminated from the skin in view of coalescence of the reconstructed skin with the mouse skin and inhibition of the reconstructed skin from constriction. Usually, the chamber is eliminated in about 2 weeks after cutting a suture thread.

Thus, a human skin tissue can be constructed from the cultured human fibroblast and the cultured human keratinocyte, or the cultured human fibroblast, the cultured human keratinocyte and the cultured human melanocyte. A factor for accelerating regeneration of skin tissue, for example, Wnt and sonic hedgehog can optionally be added in any of the steps (a) to (d). Further, a skin tissue-constituting cell such as hair folliculus and melanocyte can be added.

Figure 5:
FIG. 5 is a photograph of the exterior of reconstructed skin which is constructed on a mouse (18 weeks after grafting). (A) shows reconstructed skin containing no melanocyte, and (B) shows reconstructed skin containing melanocyte.
Figure 5:
Figure 9:
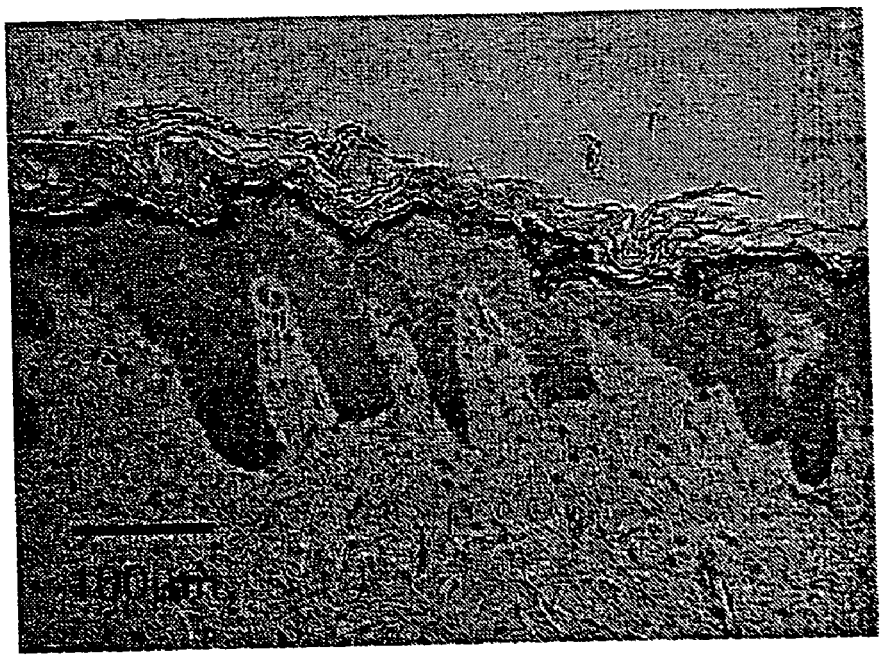
FIG. 9 is a histological observation (c-kit) of reconstructed skin. (A) is a stained tissue image obtained by using an antibody against c-kit, and (B) is a stained tissue image obtained by using non-specific IgG.
Figure 9:
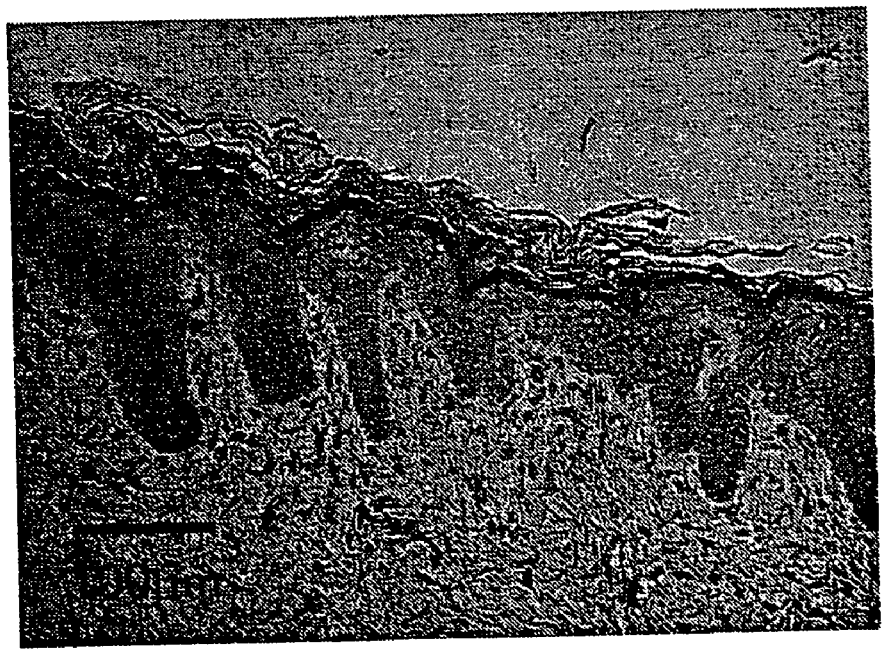
Figure 10:
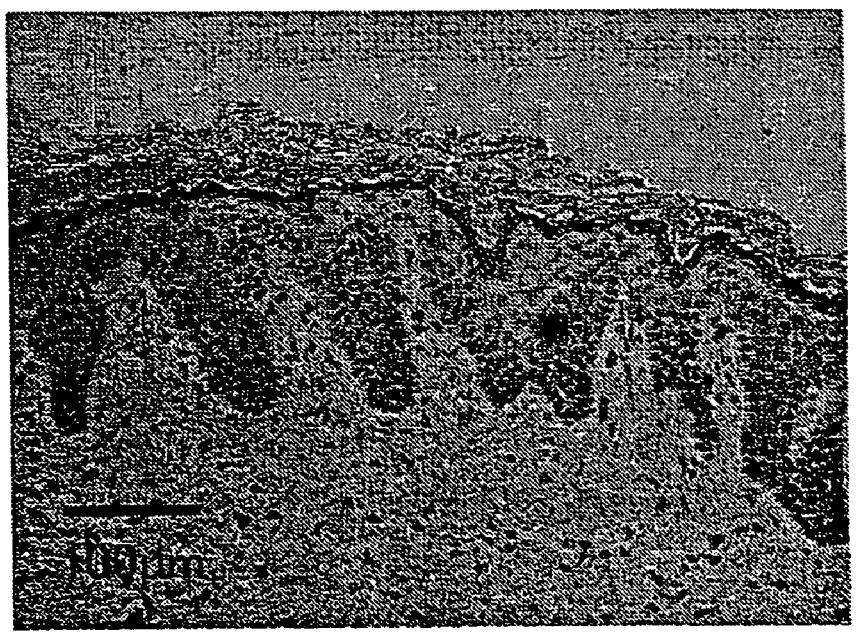
FIG. 10 is a histological observation (activated melanocyte) of reconstructed skin. (A) is a stained tissue image obtained by using an HMB 45 antibody, and (B) is a stained tissue image obtained by using non-specific IgG.
Figure 10:
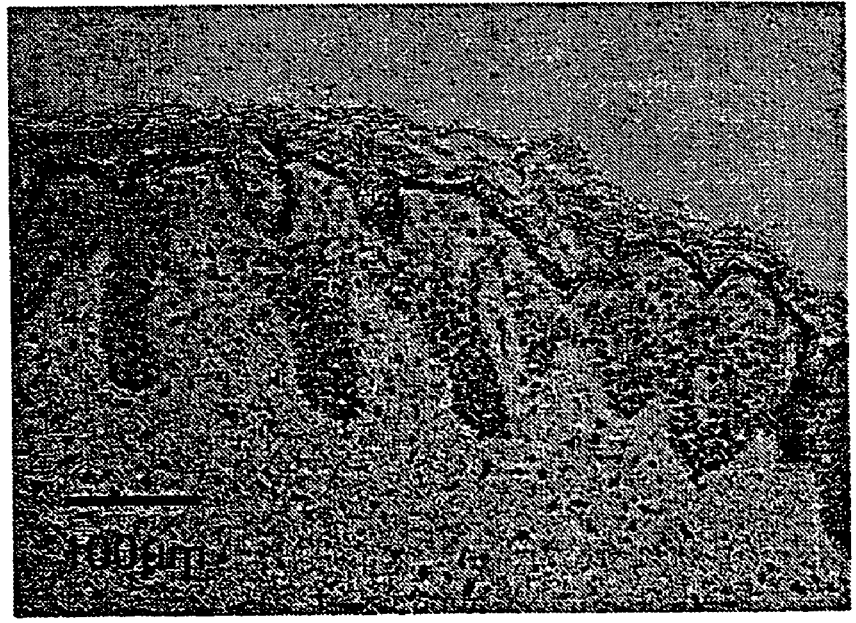
Figure 11:
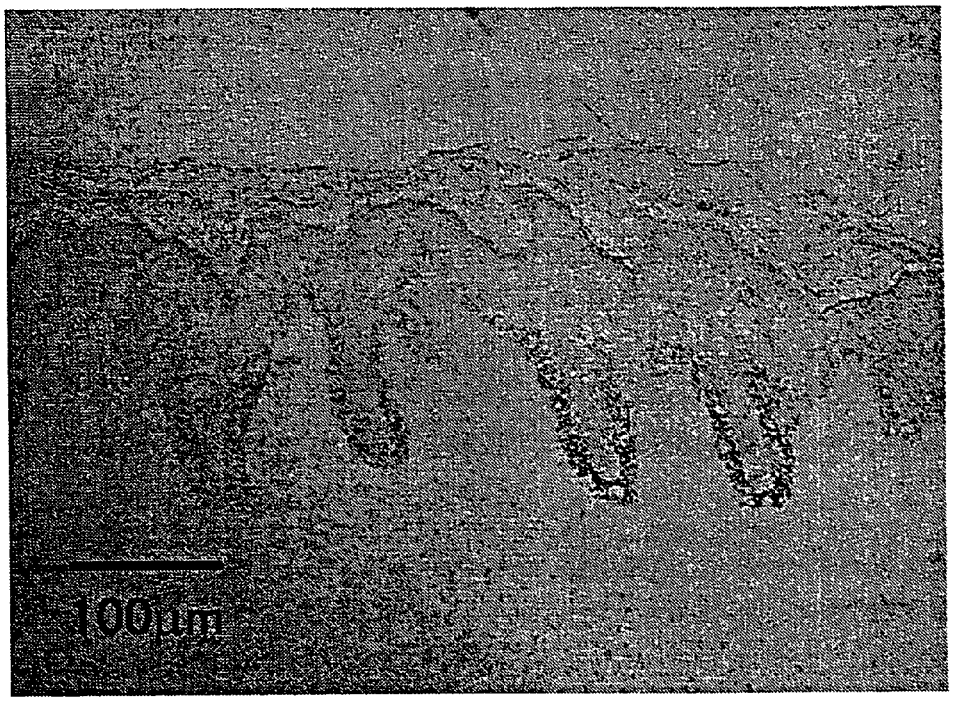
FIG. 11 is a histological observation (melanin staining (Fontana•Masson-positive staining)) of reconstructed skin.

The skin tissue reconstructed by the method of the present invention does not have scabs, has a uniform surface, and presents a gloss which is very similar to that of human skin as shown in FIG. 5. Further, it maintains at least a certain size without causing constriction. As shown in FIGS. 9 to 11, it has a base membrane structure which is very similar to that of human skin in which melanocyte is disposed. It has not so far been known that human reconstructed skin having melanocyte is constructed on the body surface of a non-human animal by a spontaneous sorting method, and this technique can provide artificial skin which can meet needs of the human races in the entire world and has a possibility of application as therapy for pigment disorder such as vulgaris vitiligo.

Accordingly, the reconstructed skin obtained by the method of the present invention can be a skin tissue model for spots, freckles, pigmentation of skin after inflammation and aged spots. Animals carrying the above skin tissue are useful not only as animals for researching genetic and protein expression in human skin but also as model animals for evaluating medicines acting on skin, particularly melanocyte, for example, medicines and lightening agents for preventing skin from darkening, and substances which are cosmetics materials such as a tanning agent. That is, a suitable amount of a test substance is administered to the animal of the present invention via an administration route such as percutaneous injecting or oral route to observe and evaluate the actions and effects thereof with the passage of time by ordinary means, whereby screening of substances acting on melanocyte and a drug action test can be carried out.

When the reconstructed skin is used, for example, for screening whitening agents, a test substance is applied on the reconstructed skin of the present invention in various concentrations to evaluate the skin color by means of a colorimeter, whereby suitability of the test substances as a whitening agent can be screened. When it is used for screening UV absorbers, the suitability of test substances as a UV absorber can be screened by measuring the epidermal hyperplasia by combining of Optical Coherence Tomography (ISIS Optronics GmbH) with Image pro 4.0 image analysis software.

The following examples further describe and demonstrate embodiments of the present invention. The examples are given solely for the purpose of illustration and are not to be construed as limitations of the present invention.

EXAMPLES

Example 1

Construction of Human Reconstructed Skin (1) Cultivation of Cell

A cultured human fibroblast (Dainippon Seiyaku Co., Ltd.) was cultured in a Dulbecco's modified Eagle's medium (Invitrogen) containing a 10% fetal bovine serum (Invitrogen Corporation) in an incubator at 37° C. with 5% $CO_2$. It was cultured in a T175 flask (FALCIN Corporation) until it reached a confluent state.

A human newborn foreskin-originating epidermal cornified cell purchased from Kurabo Co., Ltd. was used as a human cultured keratinocyte. The frozen cell was defrosted at 37° C. and then inoculated in a T25 flask (FALCON) using a keratinocyte-SFM (Invitrogen) culture medium, and was cultured in an incubator at 37° C. with 5% $CO_2$. It was subcultured in a subconfluent state, then transferred to a T175 flask and was cultured under the same condition until a subconfluent state was obtained.

A human newborn foreskin-originating epidermal pigment cell purchased from Kurabo Co., Ltd. was used as a human cultured melanocyte. The frozen cell was defrosted at 37° C., then inoculated in a T25 flask (FALCON) using a Medium 154 culture medium (Cascade Biologics Corporation), and was cultured in an incubator at 37° C. with 5% $CO_2$. It was subcultured in a subconfluent state, then transferred to a T175 flask, and was cultured under the same condition until a subconfluent state was obtained.

(2) Insertion of Chamber into Mouse

The skin on the back part of a mouse was cut in a circular form, and inserted thereinto was a chamber (combination of an upper part having an inner diameter of 12 mm and an outer diameter of 24 mm and a lower part having an inner diameter of 11 mm and an outer diameter of 24 mm) (Renner Gmbh) in which a hole having a diameter of 2 to 4 mm was provided at an upper part. The skin of the mouse at the peripheral part of the chamber was sutured just like tightening the string of a bag to fix the chamber.

(3) Injection of Cell

Recovered by centrifuging in a tube were (6-8)×$10^6$ pieces of cultured human fibroblasts peeled off by trypsin, 6×$10^6$ pieces of cultured human keratinocyte and 2×$10^5$ to 2×$10^6$ pieces of cultured human melanocyte, and the supernatant was thrown away. The recovered cells were injected into the chamber through the hole at the upper part thereof.

(4) Elimination of Chamber

One week after grafting, the upper part of the chamber was cut at a point about 5 mm below the top part, and a wire gauze was mounted thereon. The wire gauze was removed after an additional 1 to 2 weeks, and thereafter, the upper part of the chamber was completely cut. From this point in time, a physiological salt solution was applied on the reconstructed skin once every 2 to 4 days to avoid quick drying. The thread with which the chamber was sutured with the mouse was cut by means of scissors 4 to 5 weeks after grafting, and the chamber was left standing until it spontaneously detached. In general, the chamber detaches about 6 to 7 weeks after grafting.

(5) Observation of Reconstructed Skin

FIG. 5 is a photograph of the exterior of reconstructed skin. At least a certain size of the reconstructed skin was maintained, and the skin did not have scabs on the surface and was uniform. It presented a gloss very similar to that of human skin (FIG. 5 (A) and (B)). Further, the surface of the reconstructed skin containing melanocyte entirely has a brown color (FIG. 5 (B)).

Figure 6:
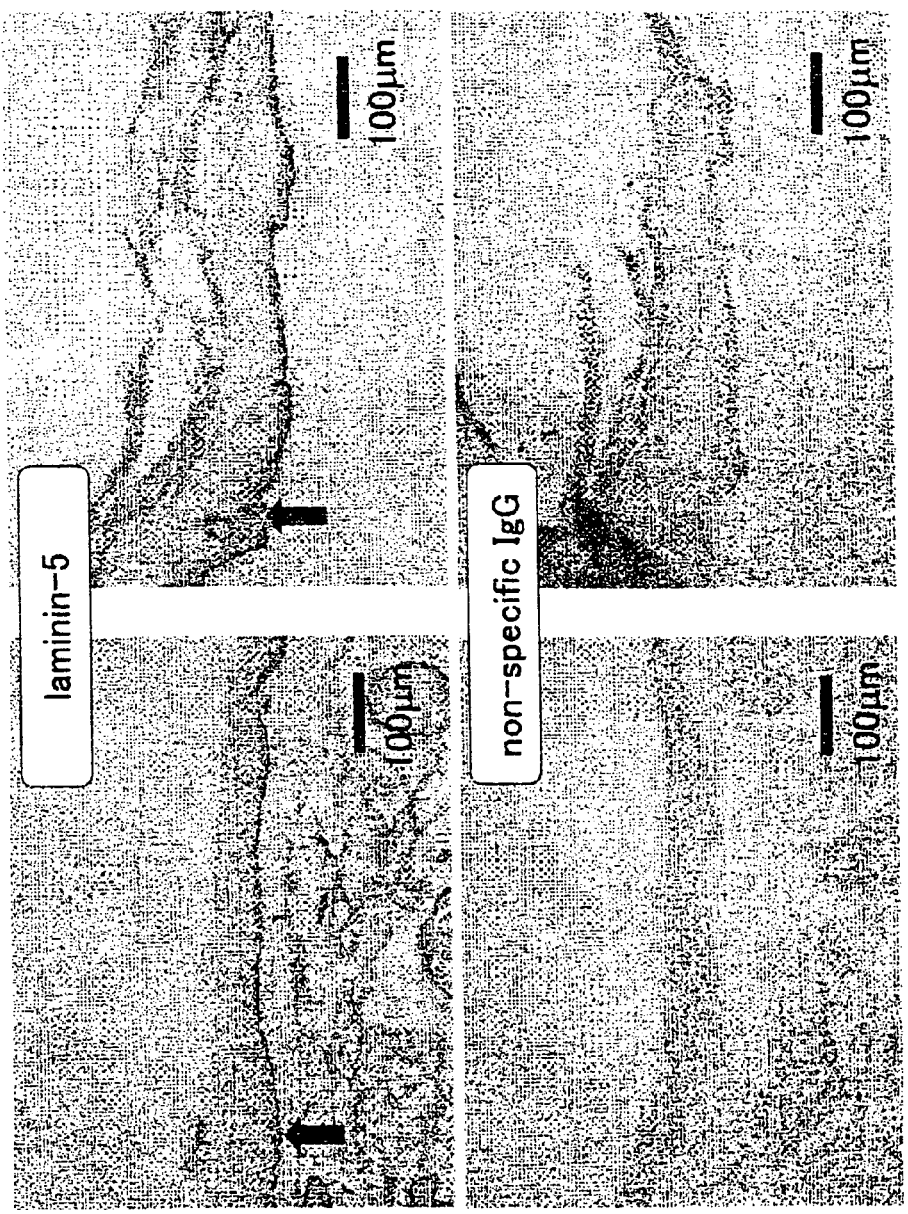
FIG. 6 is a transmission electron microphotograph of the tissue of reconstructed skin.
Figure 7:
FIG. 7 is a microphotograph of the tissue of reconstructed skin (16 weeks after grafting).

FIG. 6 shows microscopic images of the tissue intercepts of human skin (left) and the reconstructed skin (right), and immune staining was carried out using a laminin-5 antibody and a non-specific IgG antibody (negative observation). The arrow part indicates a positive observation of laminin-5 protein and shows that the same protein is expressed. The laminin-5 protein which is a constructional factor of a basement membrane zone corresponding to a connecting site between an epidermal layer and a dermal layer is also present in the reconstructed skin like in human skin, and therefore it is considered that the basement membrane zone is developed in the reconstructed skin to the same extent as in human skin. On the other hand, a positive observation is not found in the non-specific IgG antibody which is a non-specific antibody, and therefore it is shown that staining with the laminin-5 antibody is specific. Further, a lot of intermediate fibers is observed in the vicinity of the basement membrane zone in a transmission electron microphotograph of the reconstructed skin shown in FIG. 7, and therefore it is suggested that a strong basement membrane zone is formed. A white bar in the photograph shows an epidermic layer, and a black bar shows a dermal layer. It is found from FIGS. 5 to 7 that the reconstructed skin is very similar to human skin in both surface properties and internal properties.

Figure 8:
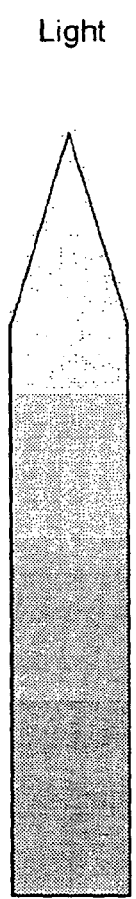
FIG. 8 is a graph showing a change in L value in the reconstructed skin after being irradiated with UVB.
Figure 8:
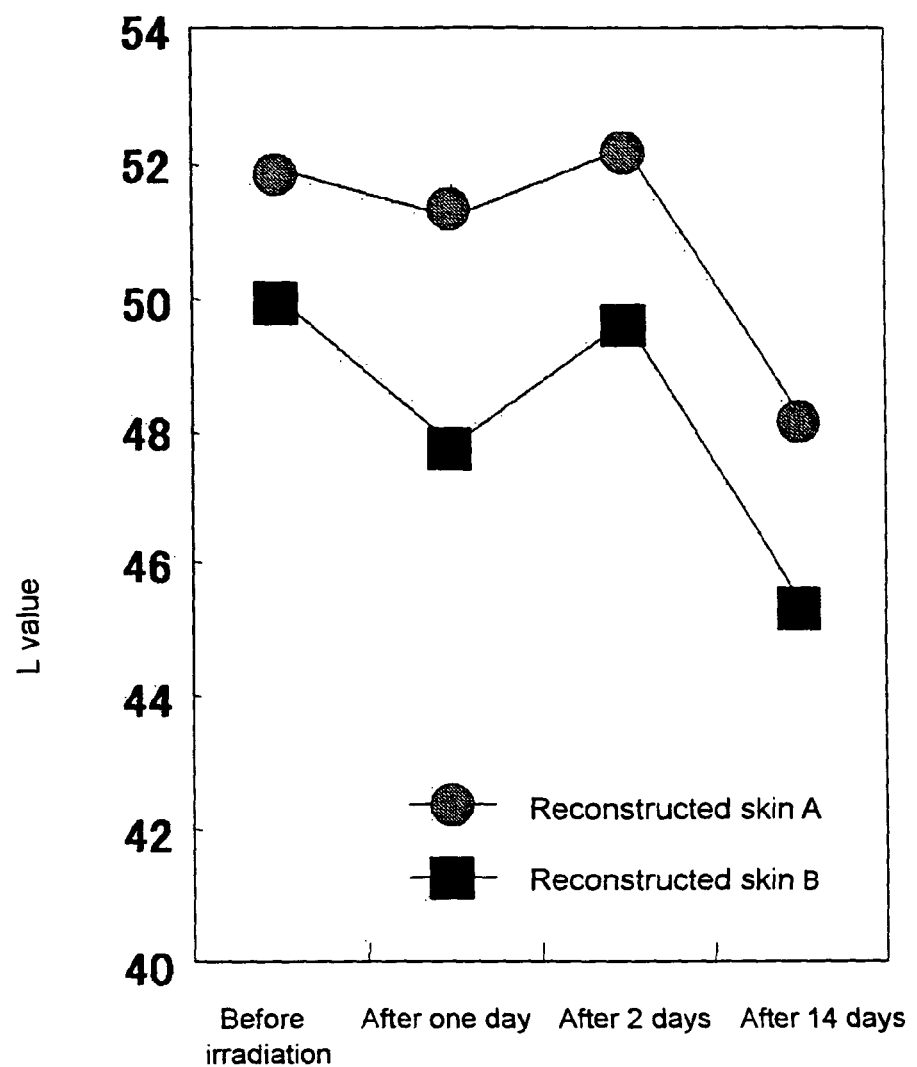

(6) Acceleration in Synthesis of Melanin by Irradiation of the Reconstructed Skin with UV Rays The reconstructed skin obtained 15 weeks after grafting onto an SCID mouse was irradiated with UV rays by means of only a UVB light source of a Toshiba FL20SE lamp. Since the epidermic keratinocyte and melanocyte used for constructing the reconstructed skin originate from a Caucasian, the skin was irradiated once with UVB of 150 mJ/$cm^2$ corresponding to double the amount of a minimum erythema dose in a Caucasian. For the purpose of measuring the blackening degree, the lightness (L value) in the central part of the reconstructed skin was measured with a color difference meter (300A manufactured by Nippon Denshoku Ind. Co., Ltd.) before irradiation with UVB, and one day, 2 days and 14 days after irradiation with UVB. It was indicated that as shown in FIG. 8, the L value was notably reduced at a point of time when 14 days passed from irradiation with UVB and it was suggested that synthesis of melanin was accelerated. In order to actually certify that the blackening degree was accelerated by an acceleration in synthesis of melanin, a paraffin intercept was prepared at a point of time when color measurement was finished 14 days after irradiation to try histological analysis thereof. An OMNITAGPLUS/HRP ACE kit (Thermo Shandon Corporation) was used as an immunohistochemical staining reagent, and therefore a positive observation was shown by a red color.

First, in order to inspect whether melanocyte was disposed in an epidermal basal layer of the reconstructed skin, an antibody (Immune Biological Institute) against c-kit which was a membrane protein specific to melanocyte was used to try the immunohistological analysis thereof. As shown in FIG. 9, a marked positive observation was found in the epidermal basal layer as compared with a stained image by non-specific IgG which was used as a reference antibody.

Next, an HMB45 antibody (DAKO Corporation) which was a marker for activated melanocyte was used to investigate whether or not melanocyte in the reconstructed skin synthesized melanin. As shown in FIG. 10, a positive observation was found in the epidermal basal layer. Further, a marked melanin pigment could be observed from the epidermal basal layer to a stratum spinosum layer above the epidermal basal layer by subjecting the intercept of the reconstructed skin to Fontana•Masson staining (FIG. 11).

(7) Epidermal Hyperplasia by Irradiation of the Reconstructed Skin with UV Rays

Figure 12:
FIG. 12 is a drawing showing epidermal hyperplasia in the reconstructed skin after being irradiated with UVB, which is taken using optical coherence tomography (OCT). The part interposed between arrows shows an epidermal thickness. (A): before irradiation with UVB; (B): one day after irradiation; (C): 2 days after irradiation; (D): 14 days after irradiation.
Figure 12:
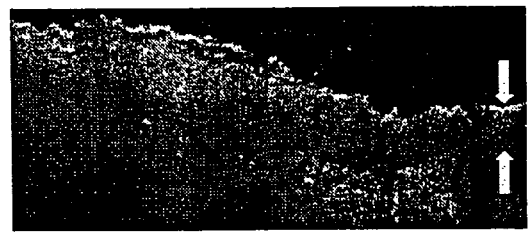
Figure 12:
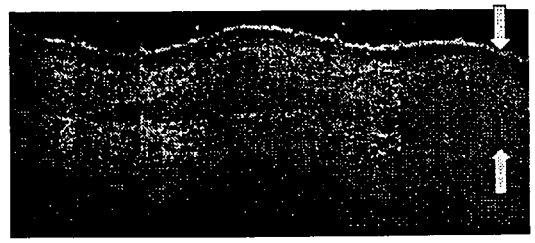
Figure 12:
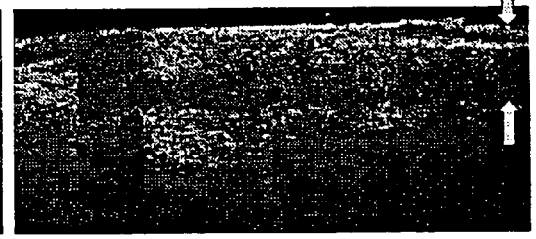
Figure 13:
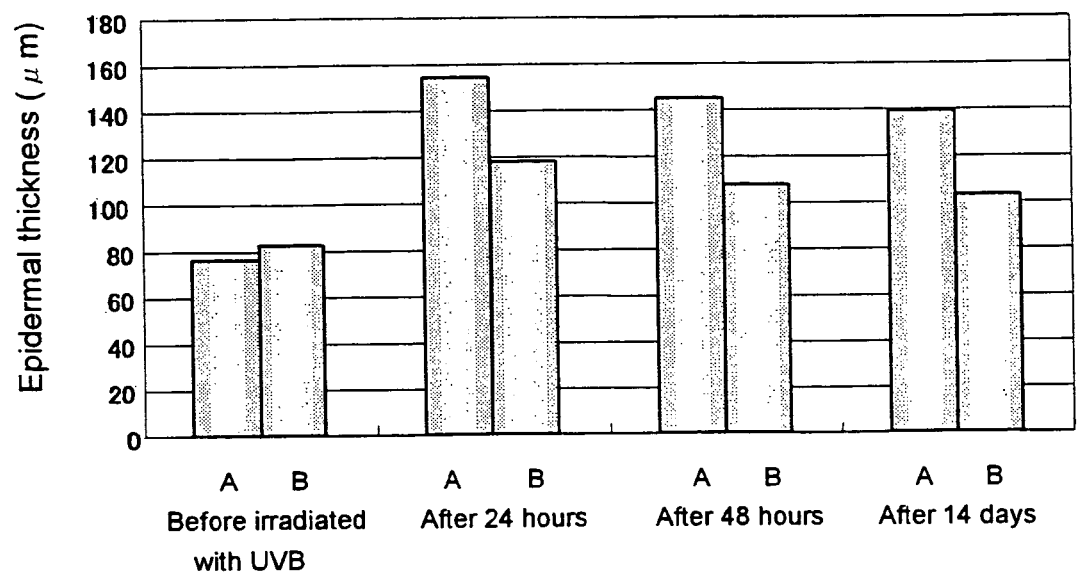
FIG. 13 is a graph showing epidermal hyperplasia in the reconstructed skin after being irradiated with UVB.

Human skin is thickened by irradiation with UV rays, and therefore it was investigated whether or not the same change was observed as well in the reconstructed skin. The epidermal hyperplasia was measured by combining Optical Coherence Tomography (ISIS Optronics GmbH) by which analysis in non-invasion was possible with an Image pro 4.0 image analysis software. Analysis with the passage of time confirmed that the epidermis was notably thickened one day after irradiation with UVB (FIG. 12 and FIG. 13). Thickening thereof was maintained even at the 14th day after irradiation with UVB.

What is claimed is:

1. A method for producing a human skin tissue, in which a human skin tissue is constructed on a body surface of an immunodeficient non-human animal, which method comprises:
   (a) grafting a cell-injectable, hat-shaped chamber (6) having a dome-shaped pan (2) and a collar part (1) into the dorsal skin of said immunodeficient non-human animal, wherein the grafting step comprises:
      (i) cutting a circular form in the dorsal skin of said immunodeficient non-human animal;
      (ii) inserting said cell-injectable, hat-shaped chamber into said dorsal skin such that the dome-shaped part of said cell-injectable, hat-shaped chamber is exposed and only the collar part is covered by said dorsal skin; and
      (iii) securing said cell-injectable, hat-shaped chamber in said dorsal skin by an adhesive or suturing;
   (b) injecting a cell suspension containing human fibroblasts and human keratinocytes into said cell-injectable, hat-shaped chamber;
   (c) at least seven days after the grafting step, cutting the dome-shaped part of said cell-injectable, hat-shaped chamber a first time such that 60% to 80% of the cross-sectional area of the dome-shaped part is open;
   (d) mounting a gas-permeable member over the opening in the dome-shaped part resulting from said first cutting;
   (e) after seven to ten days, cutting the dome-shaped part a second time such that 100% of the cross-sectional area of the dome-shaped part is open;
   (f) mounting a gas-permeable member over the opening in the dome-shaped part resulting from said second cutting; and
   (g) removing said cell-injectable, hat-shaped chamber from said immunodeficient non-human animal;
   wherein the gas-permeable membrane mounted in each of steps (d) and (f) is selected from the group consisting of gauze, a nonwoven fabric, a cloth, a metal net having a pore diameter ranging from 0.1 to 0.5 mm, a resin net having a pore diameter ranging from 0.1 to 0.5 mm, and a cotton net having a pore diameter ranging from 0.1 to 0.5 mm.

2. The method according to claim 1, wherein said first cutting of step (c) is such that 70% of the cross-sectional area of the dome-shaped part is open.

3. The method according to claim 1, wherein said securing is by suturing; and wherein the method further comprises, after the second cutting of step (e), applying a physiological salt solution to the cells once every two to four days.

4. The method according to claim 3, wherein said suturing is performed utilizing a suture thread and said suture thread is cut 14 to 21 days after suturing to enable said removing.

5. The method according to claim 1, wherein said first cutting of step (c) is performed seven to ten days after said injecting.

6. The method according to claim 1, wherein said removing is performed 28 to 56 days after said second cutting of step (e).

7. The method according to claim 1, wherein said removing is performed 28 to 35 days after said second cutting of step (e).

8. A method for producing a human skin tissue, in which a human skin tissue is constructed on a body surface of an immunodeficient non-human animal, which method comprises:
   (a) grafting a cell-injectable, hat-shaped chamber (6) having a dome-shaped pan (2) and a collar part (1) into the dorsal skin of said immunodeficient non-human animal, wherein the grafting step comprises:
      (i) cutting a circular form in the dorsal skin of said immunodeficient non-human animal;
      (ii) inserting said cell-injectable, hat-shaped chamber into said dorsal skin such that the dome-shaped part of said cell-injectable, hat-shaped chamber is exposed and only the collar part is covered by said dorsal skin; and
      (iii) securing said cell-injectable, hat-shaped chamber in said dorsal skin by an adhesive or suturing;
   (b) injecting a cell suspension containing human fibroblasts, human keratinocytes, and human melanocytes into said cell-injectable, hat-shaped chamber;
   (c) at least seven days after the grafting step, cutting the dome-shaped part of said cell-injectable, hat-shaped chamber a first time such that 60% to 80% of the cross-sectional area of the dome-shaped part is open;
   (d) mounting a gas-permeable member over the opening in the dome-shaped part resulting from said first cutting;
   (e) after seven to ten days, cutting the dome-shaped part a second time such that 100% of the cross-sectional area of the dome-shaped part is open;
   (f) mounting a gas-permeable member over the opening in the dome-shaped part resulting from said second cutting; and
   (g) removing said cell-injectable, hat-shaped chamber from said immunodeficient non-human animal;
   wherein the gas-permeable membrane mounted in each of steps (d) and (f) is selected from the group consisting of gauze, a nonwoven fabric, a cloth, a metal net having a pore diameter ranging from 0.1 to 0.5 mm, a resin net having a pore diameter ranging from 0.1 to 0.5 mm, and a cotton net having a pore diameter ranging from 0.1 to 0.5 mm.

9. The method according to claim 8, wherein said first cutting of step (c) is such that 70% of the cross-sectional area of the dome-shaped part is open.

10. The method according to claim 8, wherein said securing is by suturing, and wherein the method further comprises, after the second cutting of step (e), applying a physiological salt solution to the cells once every two to four days.

11. The method according to claim 10, wherein said suturing is performed utilizing a suture thread and said suture thread is cut 14 to 21 days after suturing to enable said removing.

12. The method according to claim 8, wherein said first cutting of step (c) is performed seven to ten days after said injecting.

13. The method according to claim 8, wherein said removing is performed 28 to 56 days after said second cutting of step (e).

14. The method according to claim 8, wherein said removing is performed 28 to 35 days after said second cutting of step (e).

* * * * *

UNITED STATES PATENT AND TRADEMARK OFFICE
CERTIFICATE OF CORRECTION

PATENT NO. : 7,736,894 B2  Page 1 of 1
APPLICATION NO. : 10/847380
DATED : June 15, 2010
INVENTOR(S) : Akira Hachiya et al.

It is certified that error appears in the above-identified patent and that said Letters Patent is hereby corrected as shown below:

In column 9, line 10, "pan" should read -- part --.

In column 10, line 6, "pan" should read -- part --.

Signed and Sealed this

Fourteenth Day of September, 2010

David J. Kappos
*Director of the United States Patent and Trademark Office*